US010292687B2

(12) United States Patent
Maguire et al.

(10) Patent No.: US 10,292,687 B2
(45) Date of Patent: May 21, 2019

(54) DESIGNS AND METHODS TO FACILITATE SWALLOWING OF A TETHERED CELL COLLECTION DEVICE

(71) Applicant: COVIDIEN LP, Mansfield, MA (US)

(72) Inventors: Mark A. Maguire, Hillsborough, CA (US); Alexander A. Lubinski, Rocklin, CA (US); Jeevan Maddur Shankarsetty, Bangalore (IN); Vijayaraghavan Srinivasan Chari, Secunderabad Andhrapradesh (IN); Neeraj Eswaradas, Kerala (IN); Yogesh Kishor Vikharankar, Maharashtra (IN); Narsing Sairaj Bheemarthi, Hyderabad (IN); Ananta Venkata Varaha Lakshmi Narasimha Srinivasa Murthy Aravalli, West Godavari (IN); Inderjeet S. Bhalla, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 777 days.

(21) Appl. No.: 14/826,426

(22) Filed: Aug. 14, 2015

(65) Prior Publication Data
US 2016/0045189 A1 Feb. 18, 2016

Related U.S. Application Data

(60) Provisional application No. 62/037,669, filed on Aug. 15, 2014.

(51) Int. Cl.
*A61B 10/02* (2006.01)

(52) U.S. Cl.
CPC ...... *A61B 10/02* (2013.01); *A61B 2010/0216* (2013.01)

(58) Field of Classification Search
CPC ..... A61B 1/041; A61B 5/073; A61B 1/00158; A61B 1/00016; A61B 10/02
See application file for complete search history.

(56) References Cited

U.S. PATENT DOCUMENTS

| 5,947,118 | A | * | 9/1999 | Hochrainer | ....... | A61M 15/0028 128/203.12 |
| 7,295,226 | B1 | * | 11/2007 | Meron | ............... | A61B 1/00036 348/77 |
| 2007/0161851 | A1 | * | 7/2007 | Takizawa | ........... | A61B 1/00156 600/102 |
| 2011/0031150 | A1 | * | 2/2011 | Trigg | .................. | B65D 75/366 206/461 |
| 2012/0226189 | A1 | * | 9/2012 | Fitzgerald | .............. | A61B 10/02 600/562 |

* cited by examiner

*Primary Examiner* — Sean P Dougherty
*Assistant Examiner* — Patrick Fernandes

(57) ABSTRACT

Methods, apparatuses and systems are described for administering a swallowable cell collection device to a patient. Methods include releasing a swallowable bundle of string of the cell collection device from a bundling apparatus, maintaining the string in a swallowable bundle while releasing the swallowable bundle from the bundling apparatus, and placing the swallowable bundle on the tongue of the patient. Methods also include constraining a retrieval string of the cell collection device in a swallowable bundle with a dissolvable band and placing the swallowable bundle on the tongue of the patient.

6 Claims, 20 Drawing Sheets

DESIGNS AND METHODS TO FACILITATE SWALLOWING OF A TETHERED CELL COLLECTION DEVICE

CROSS REFERENCES

The present application claims the benefit of and priority to U.S. Provisional Application No. 62/037,669, entitled "Designs and Methods to Facilitate Swallowing of a Tethered Cell Collection Device," filed on Aug. 15, 2014, the entire contents of which are expressly incorporated herein.

BACKGROUND

To diagnose certain diseases of the gastrointestinal tract, a swallowable cell collection device may be used to collect cells from the surface of the gastrointestinal tract of a patient. Typically, a swallowable cell collection device will include a retrieval string that allows the swallowable portion of the cell collection device to be retrieved back through the mouth of the patient. However, swallowing the retrieval string may be very difficult and unpleasant for the patient because the string may trigger the patient's gag reflex.

Accordingly, there may be a need for improved methods and devices to administer a swallowable cell collection device with a retrieval string to a patient.

SUMMARY

The described features generally relate to one or more improved methods, systems, or apparatuses for administering a swallowable cell collection device to a patient. According to various embodiments, packaging apparatuses include one or more features or materials configured to house components of the swallowable cell collection device while the cell collection device is in a pre-deployed configuration. Some features of the packaging apparatuses are configured to releasably retain a string of the swallowable cell collection device in a swallowable bundle. Improved methods include removing a swallowable bundle of string of the cell collection device from a packaging apparatus while maintaining the string in a swallowable bundle and delivering the swallowable bundle to a patient.

According to various embodiments, a packaging apparatus for administering a swallowable cell collection device to a patient is provided. In general, a packaging apparatus may include one or more bundling features configured to releasably retain a portion of retrieval string of a swallowable cell collection device in a swallowable bundle. The packaging apparatus may further include a capsule housing configured to releasably retain a swallowable capsule of the swallowable cell collection device.

Additionally or alternatively, one or more of the bundling features may include one or more shafts with a proximal end coupled with the packaging apparatus and a distal end opposite the proximal end. The packaging apparatus may also include two shafts arranged parallel to each other. One or more shafts may be tapered such that a distal end of the shaft has a smaller cross section than a proximal end of the shaft.

In some embodiments, one or more of the shafts included in the packaging apparatus may contain a distal end retaining member coupled with the distal end and configured to prevent the swallowable bundle from sliding off the distal end while the swallowable cell collection device is in a pre-deployed configuration. Furthermore, the distal retaining member is removable in some examples.

In certain aspects, one or more bundling features may contain two posts extending orthogonal to a planar surface of the packaging apparatus. Furthermore, the packaging apparatus may contain a scoring feature disposed on a surface of the packaging apparatus and configured to facilitate bending of the packaging apparatus along the scoring feature. The retrieval string may be treated such that it remains bundled in the absence of external constraining forces.

In some embodiments, the packaging apparatus may contain a swallowable cell collection device, the swallowable cell collection device comprising a swallowable capsule coupled with a retrieval string, wherein the retrieval string is wrapped around the one or more bundling features in a swallowable bundle and the swallowable capsule is releasably retained in the capsule housing.

In yet another embodiment, a packaging apparatus for administering a swallowable cell collection device to a patient may comprise a swallowable cell collection device, the swallowable cell collection device comprising a swallowable capsule coupled with a retrieval string. Additionally or alternatively, such an embodiment may also include a capsule housing configured to releasably retain the swallowable capsule. A bundling material may be configured to releasably retain a portion of the retrieval string in a swallowable bundle. The bundling material may be a band wrapped around the swallowable bundle. Furthermore, the bundling material may be coupled with the packaging apparatus. In some embodiments, the bundling material may be dissolvable such that it dissolves when placed in contact with liquid. Additionally, the bundling material may comprise a pull tab, and the bundling material may further comprise a perforation.

According to various embodiments, a method for administering a swallowable cell collection device to a patient is provided. The method may include providing a packaging apparatus with a swallowable cell collection device, the swallowable cell collection device comprising a swallowable capsule coupled with a retrieval string, wherein the swallowable capsule is releasably retained in a capsule housing coupled with the packaging apparatus and a portion of the retrieval string is releasably retained in a swallowable bundle by one or more bundling features or bundling materials. Such a method may also include removing the swallowable bundle from the one or more bundling features or bundling materials while maintaining the swallowable bundle in a bundled configuration. In some embodiments, the method also includes placing the swallowable bundle on the tongue of the patient.

According to some embodiments, one or more bundling features may comprise one or more shafts around which the retrieval string is wound to form the swallowable bundle, and wherein removing the swallowable bundle from the one or more bundling features comprises sliding the swallowable bundle from a distal end of the one or more shafts. In such a method, one or more bundling materials may comprise a band wrapped around the swallowable bundle, and removing the swallowable bundle from the bundling material may comprise tearing the band.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Typically, a swallowable cell collection device used to diagnose certain diseases of the gastrointestinal tract will include a swallowable portion and a retrieval string coupled with the swallowable portion such that the swallowable portion may be retrieved back through the mouth of the patient. However, swallowing the retrieval string can be difficult or unpleasant for the patient because the presence of the string extending down the patient's throat can trigger the patient's gag reflex. Therefore, methods of administering the retrieval string to the patient in a compact yet swallowable configuration are described herein.

Additionally, a cell collection device packaged in such a way that requires the user to unwrap the retrieval string from the packaging and then to rewrap or otherwise manipulate the retrieval string before administering the cell collection device to the patient is cumbersome and tedious to prepare and administer. Requiring the user to manually bundle the retrieval string before administering the device to the patient could increase the potential that the retrieval string will become tangled, increases the time required to perform the procedure, and reduces the uniformity with which this type of procedure is performed across multiple patients. Accordingly, apparatuses configured to administer a swallowable cell collection device without requiring a user to unwrap and then manually rewrap or bundle the retrieval string are described herein.

Figure 1A:
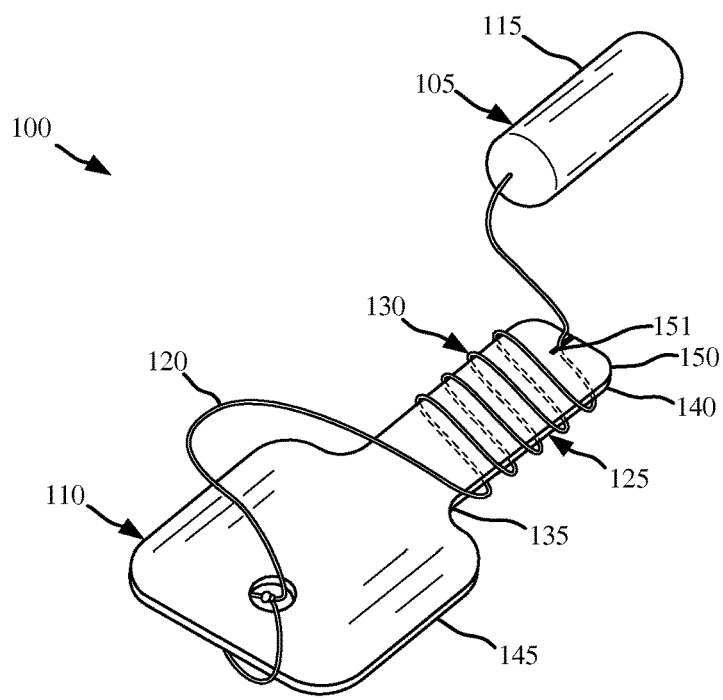
FIGS. 1A and 1B are schematic diagrams of a packaging apparatus and a swallowable cell collection device according to various embodiments.

FIG. 1A illustrates an example of a packaged cell collection device assembly 100. In general, a packaged cell collection device assembly may include a swallowable cell collection device 105 and a packaging apparatus 110. According to various embodiments, the packaging apparatus 110 is configured to retain the cell collection 105 in a pre-deployed or packaged configuration until the cell collection device 105 is ready for use on a patient. The swallowable cell collection device 105 is shown in a pre-deployed configuration in FIG. 1A. A pre-deployed configuration refers to the cell collection device 105 being stored or packaged before being administered to a patient. In a pre-deployed configuration, the cell collection device 105 may be attached or coupled with the packaging apparatus 110 in a variety of ways as explained in further detail below. For example, the cell collection device 105 may be wrapped around a portion of the packaging apparatus 110 and may be retained in place by one or more retention features such as a slit, a removable tab, a hook or any combination of these features.

In general, the cell collection device 105 includes a swallowable capsule 115 coupled with a retrieval string 120. The swallowable capsule 115 may contain an expandable sponge (not shown) or other similar material or device configured to collect cells from the stomach or esophagus of the patient. The string 120 may be tied or otherwise coupled with the packaging apparatus 110 at one end and coupled with the expandable sponge contained within swallowable capsule 115 at the other end.

The retrieval string 120 may be made from one or more natural or synthetic materials. For example, surgical suture material may be used. The string 120 is configured to be swallowed by a patient along with the swallowable capsule 115. In some embodiments, the string 120 is coated or otherwise treated to make the surface of the string 120 more slippery and easier to swallow and withdraw. Additionally, the string 120 may also be coated or otherwise treated to manipulate the elasticity and resilience of the string 120. For example, the string 120 may be heat treated such that the string 120 retains a desired shape or configuration (such as a swallowable bundle) in the absence of external constraints or forces. Furthermore, the length of the string 120 is selected to allow the swallowable capsule 115 to enter the stomach of a patient and to be retrieved back through the esophagus of the patient.

When the cell collection device 105 is in a pre-deployed configuration, the string 120 is maintained in a swallowable bundle 130 by one or more bundling apparatuses, features, materials, or other bundling means. The bundling apparatuses, features, or materials may be a feature or component of the packaging apparatus 110 or a separate element as explained in more detail below.

A swallowable bundle 130 refers to a bundle of retrieval string 120 with a size and shape that can be easily placed on the tongue of a patient and swallowed by the patient. As a patient swallows the swallowable bundle 130, the string 120 naturally unbundles and straightens out within the esophagus while the swallowable capsule 115 travels down the esophagus of the patient.

Figure 12:
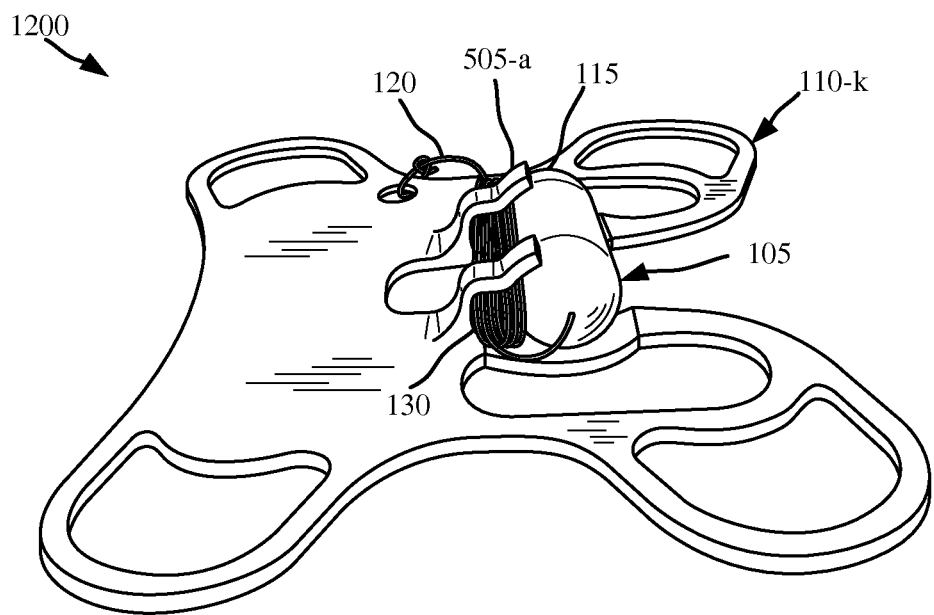
FIG. 12 is a schematic diagram of a packaging apparatus and a swallowable cell collection device according to various embodiments.
Figure 13:
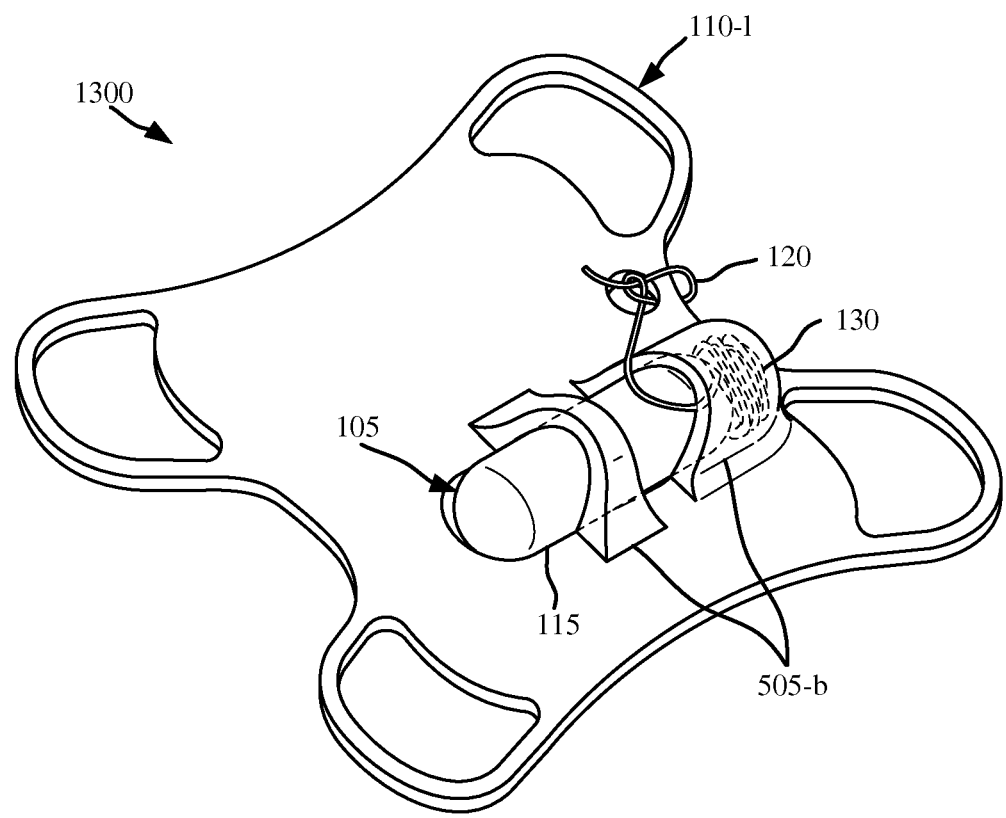
FIG. 13 is a schematic diagram of a packaging apparatus and a swallowable cell collection device according to various embodiments.

A bundle 130 of string 120 may be formed by wrapping a portion of the string 120 around one or more bundling features such as one or more shafts, posts, or some other portion of the packaging apparatus 110. For example, a portion of string 120 may be helically wrapped around a shaft 125 of the packaging apparatus 110 to form a swallowable bundle 130. The shaft 125 may be substantially planar with a generally rectangular cross section. In other embodiments, such as FIG. 2, the shaft 125 may be rounded with a circular or oval cross section. Moreover, in some embodiments, the string 120 is wrapped around multiple shafts 125 to form a swallowable bundle 130. In general, the shape and size of shaft 125 is configured to facilitate the formation of a swallowable bundle 130 of string 120 with a length and cross sectional dimension to allow the bundle 130 to be placed on the tongue of a patient and swallowed. In other embodiments, the swallowable bundle 130 may be formed by looping or folding the string 120 back on itself multiple times, as shown in FIG. 12. In yet other embodiments, the string 120 may be formed into a swallowable bundle 130 by wrapping the string 120 into a cylindrical or spherical shape as shown in FIG. 13.

The packaging apparatus 110 may include features to retain the cell collection device 105 and to prevent the swallowable bundle 130 from becoming unbundled when the cell collection device 105 is in a pre-deployed configuration. For example the shaft 125 may include retaining members that constrain the swallowable bundle 130 in a bundled configuration. The proximal end 135 of the shaft 125 may include a proximal end retaining member 145. The proximal end retaining member 145 is configured to prevent the swallowable bundle 130 from sliding off the proximal end 135 of shaft 125. As shown in FIG. 1, the proximal end retaining member 145 comprises a portion with a larger cross section than that of the shaft 125. Accordingly, when the swallowable bundle 130 is wrapped around the shaft 125, it is prevented from sliding off the proximal end 135 of shaft 125 by the proximal end retaining member 145.

Similarly, the distal end 140 of the shaft 125 may include a distal end retaining member 150 configured to prevent the swallowable bundle 130 from sliding off the distal end 140 of the shaft 125 when the cell collection device 105 is in a pre-deployed configuration. In some embodiments, the distal end retaining member 150 includes a slit 151 cut into the distal end retaining member 150. The width and depth of the slit 151 is configured to grasp the string 120, thereby preventing the swallowable bundle 130 from unbundling or sliding off the distal end 140 of shaft 125 while in a pre-deployed configuration.

Figure 1B:
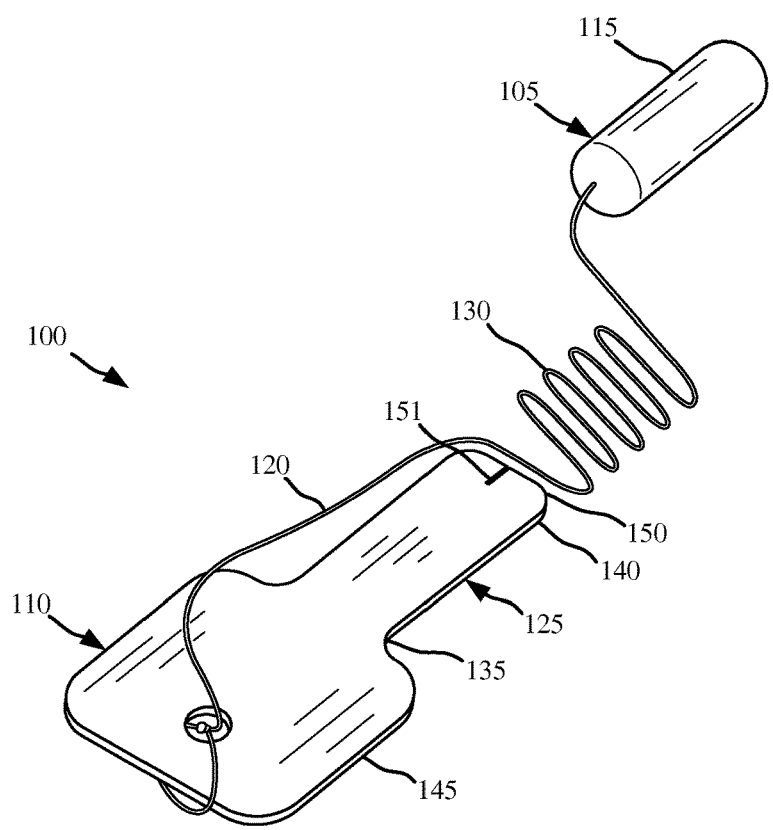

FIG. 1B shows the packaged cell collection device assembly 100 with the cell collection device 105 in a deployed configuration. The cell collection device 105 is in a deployed configuration when it is ready to be administered to the patient. For example, the cell collection device 105 may be transitioned from a pre-deployed configuration to a deployed configuration by removing, detaching, or otherwise decoupling at least a portion of the cell collection device 105 from at least a portion of the packaging apparatus 110. In some embodiments, the swallowable bundle 130 is released from a bundling feature, material, apparatus, or other bundling means when the cell collection device 105 is in a deployed configuration. For example, the cell collection device 105 may be deployed by sliding the swallowable bundle 130 off the distal end 140 of shaft 125. Additionally or alternatively, the cell collection device 105 is transitioned from a pre-deployed configure to a deployed configuration by removing the swallowable capsule 115 from a capsule retention member such as a capsule housing, as described in more detail below.

In general, the packaging apparatus 110 and the retention and bundling features are configured such that there is no need to re-bundle the string 120 into a swallowable bundle 130 once removed from the packaging apparatus 110. As the swallowable bundle 130 is removed from the shaft 125, a user may retain the swallowable configuration by grasping the bundle 130 between two fingers, such as the thumb and index finger, or by using tweezers or any other suitable grasping device. In embodiments where the string 120 has been heat treated, the string 120 will remain in a substantially bundled configuration in the absence of external constraining forces from the shaft 125, retaining members 145, 150, or the user. The swallowable bundle 130 can then be administered to the patient by carefully placing the swallowable bundle 130 on the patient's tongue.

Figure 2:
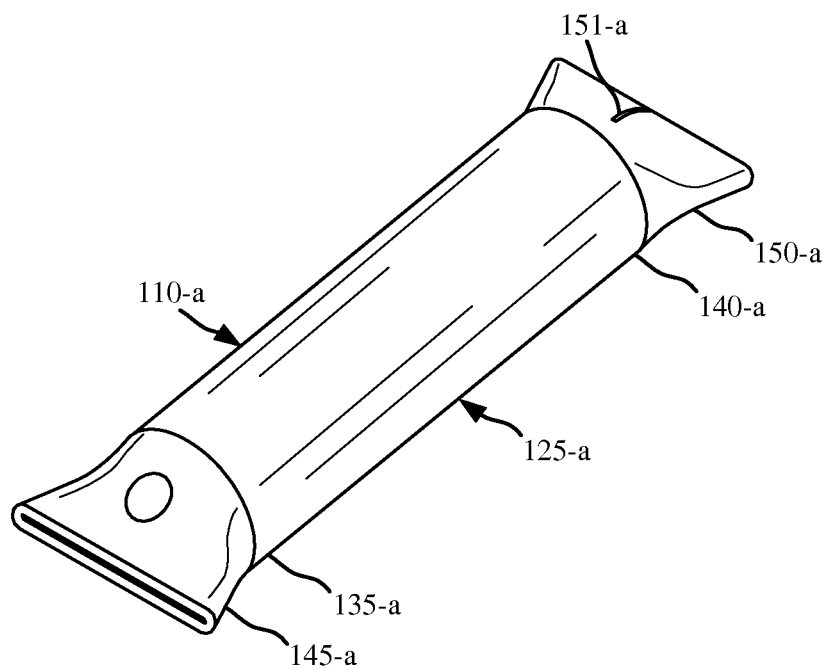
FIG. 2 is a schematic diagram of a packaging apparatus according to various embodiments.

FIG. 2 shows an example of a packaging apparatus 110-*a*, which may be an example of packaging apparatus 110 from FIG. 1. The packaging apparatus 110-*a* may include a shaft 125-*a* around which a string 120 (not shown) of a cell collection device 105 (not shown) may be wrapped into a swallowable bundle 130. The shaft 125-*a* includes a proximal end 135-*a* and a distal end 140-*a*. Each end may include a retaining member configured to retain the swallowable bundle 130 (not shown) in a bundled configuration and to prevent the swallowable bundle 130 from sliding off either end of the shaft 125-*a*. For example, the proximal end retaining member 145-*a* may include a flared portion such that the cross section of proximal end retaining member 145-*a* is greater than a cross section of the shaft 125-*a*. The increased cross section of proximal end retaining member 145-*a* will prevent the swallowable bundle 130 from sliding off the proximal end 135-*a*.

Similarly, the distal end 140-*a* of the shaft 125-*a* may include a distal end retaining member 150-*a* to prevent the swallowable bundle 130 from sliding off the distal end 140-*a* of the shaft 125-*a*. The distal end retaining member 150-*a* may include a slit 151-*a* cut into the distal end retaining member 150-*a*. As described in relation to FIG. 1, the slit 151-*a* is configured to grasp a portion of string 120 to help prevent the swallowable bundle 130 from sliding off the distal end 140-*a*. Additionally, the distal end retaining member 150-*a* may be flared to keep the swallowable bundle 130 from sliding off the distal end 140-*a* of the shaft 125-*a*. To remove the swallowable bundle 130 from the shaft 125-*a*, a user must pull on the bundle 130 with sufficient force to remove the string 120 from slit 151-*a* and to stretch the string 120 over the flared portion of distal end retaining member 150-*a*.

Figure 3:
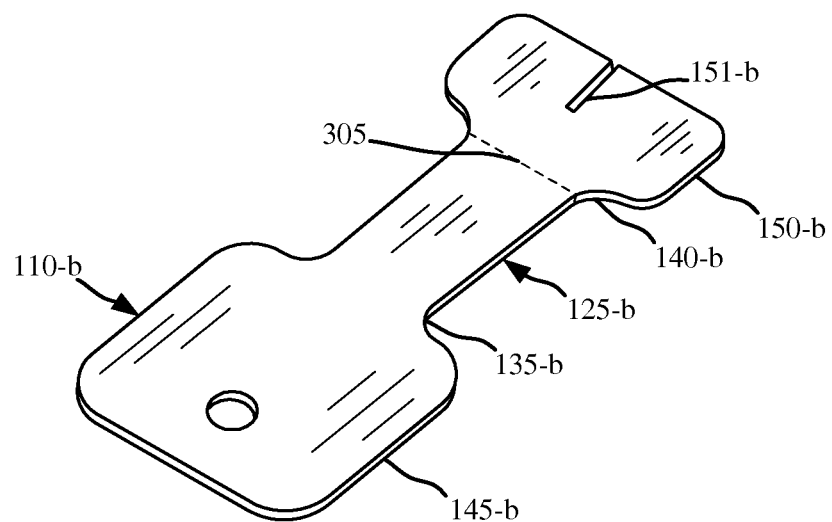
FIG. 3 is a schematic diagram of a packaging apparatus according to various embodiments.

FIG. 3 illustrates another example of a packaging apparatus 110-*b* according to various aspects of the present disclosure configured to administer a swallowable cell collection device 105 to a patient. The packaging apparatus 110-*b* includes a shaft 125-*b* around which a string 120 (not shown) of a swallowable cell collection device 105 (not shown) may be wrapped into a swallowable bundle 130 (not shown). The packaging apparatus 110-*b* may be an example of a packaging apparatus 110 described in connection with any of FIGS. 1-2. The shaft 125-*b* includes a proximal end 135-*b* and a distal end 140-*b*. Each end may include a retaining member configured to prevent a swallowable bundle 130 of string 120 from sliding off either end of shaft 125-*b*. For example, the proximal end retaining member 145-*b* may include a portion with a larger cross section than that of the shaft 125-*b*. The larger cross section of proximal end retaining member 145-*b* will keep the swallowable bundle 130 from sliding off the proximal end 135-*b*.

The packaging apparatus 110-*b* may also include a distal end retaining member 150-*b* coupled with the distal end 140-*b* of the shaft 125-*b*. Similar to the proximal end retaining member 145-*b*, distal end retaining member 150-*b* is configured to prevent a swallowable bundle 130 of string 120 from sliding off the distal end 140-*b* when the cell collection device 105 is in a pre-deployed configuration. Distal end retaining member 150-*b* may have a larger cross section than that of shaft 125-*b* to help keep the swallowable bundle 130 from sliding off the distal end 140-*b*. Additionally, distal end retaining member 150-*b* may include a slit 151-*b* configured to grasp a portion of the retrieval string 120 of the swallowable cell collection device 105.

In certain aspects of the present disclosure, the distal end retaining member 150-*b* may be configured to be removable from the shaft 125-*b*. For example, the material and dimensions of the distal end retaining member 150-*b* may be chosen such that the distal end retaining member 150-*b* can be easily torn away from the shaft 125-*b*. In some examples, a perforation 305 is included in the distal end 140-*b* of the shaft 125-*b* to facilitate the removal of the distal end retaining member 150-*b*.

Figure 4:
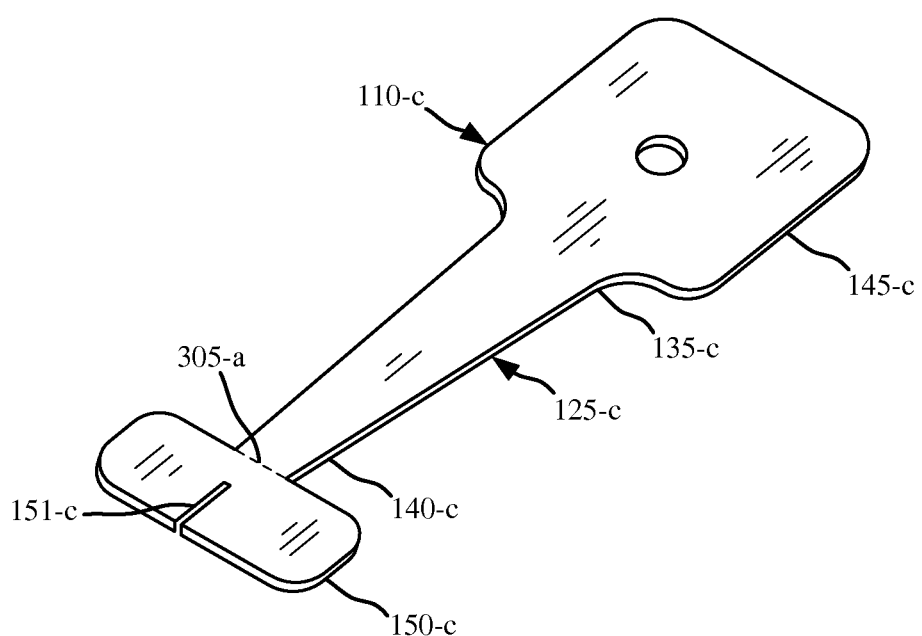
FIG. 4 is a schematic diagram of a packaging apparatus according to various embodiments.

In other embodiments, the shape of the shaft 125 is configured to facilitate the formation and retention of a more compact swallowable bundle 130 of string 120 of the cell collection device 105. For example, FIG. 4 shows a packaging apparatus 110-*c* with a tapered shaft 125-*c*. The packaging apparatus 110-*c* may be an example of packaging apparatuses 110 described with reference to any of FIGS. 1-3. The tapered shaft 125-*c* is configured to have a smaller cross section at the distal end 140-*c* of the shaft 125-*c* than that of the proximal end 135-*c*. The tapered shaft 125-*c* facilitates the creation of a compact swallowable bundle 130 (not shown) of string 120 (not shown) by urging the bundle 130 towards the distal end 140-*c*.

The packaging apparatus 110-*c* may also include a proximal end retaining member 145-*c* and a distal end retaining member 150-*c* configured to prevent the swallowable bundle 130 of string 120 from sliding off either end of the shaft 125-*c*. Similar to the proximal end retaining members described in connection with FIGS. 1-3, proximal end retaining member 145-*c* includes a larger cross section than that of shaft 125-*c* to prevent the swallowable bundle 130 from sliding off the proximal end 135-*c*. Similar to the distal end retaining member 150-*b* described in connection with FIG. 3, distal end retaining member 150-*c* may be releasably attached to the distal end 140-*c* of shaft 125-*c*. In some embodiments, the material and dimensions of distal end 140-*c* are configured to allow the distal end retaining member 150-*c* to be torn from shaft 125-*c*. In certain aspects, a perforation 305-*a* is included in the distal end 140-*c* of shaft 125-*c* to facilitate removal of the distal end retaining member 150-*c*. Furthermore, distal end retaining member 150-*c* may also include a slit 151-*c* configured to grasp a portion of the retrieval string 120.

Any of the packaging apparatuses 110 describe in connection with FIGS. 1-4 may be further configured to serve functions in addition to retaining a portion of the string 120 in a swallowable bundle 130 while the cell collection device 105 is in a pre-deployed configuration. For example, the packaging apparatus 110 may include one or more housing members to releasably retain the swallowable capsule 115 or the swallowable bundle 130 of string 120 or both. Additionally, the packaging apparatus 110 may be sized to prevent the retrieval string 120 of the cell collection device 105 from being lost down the esophagus of a patient.

Figure 5A:
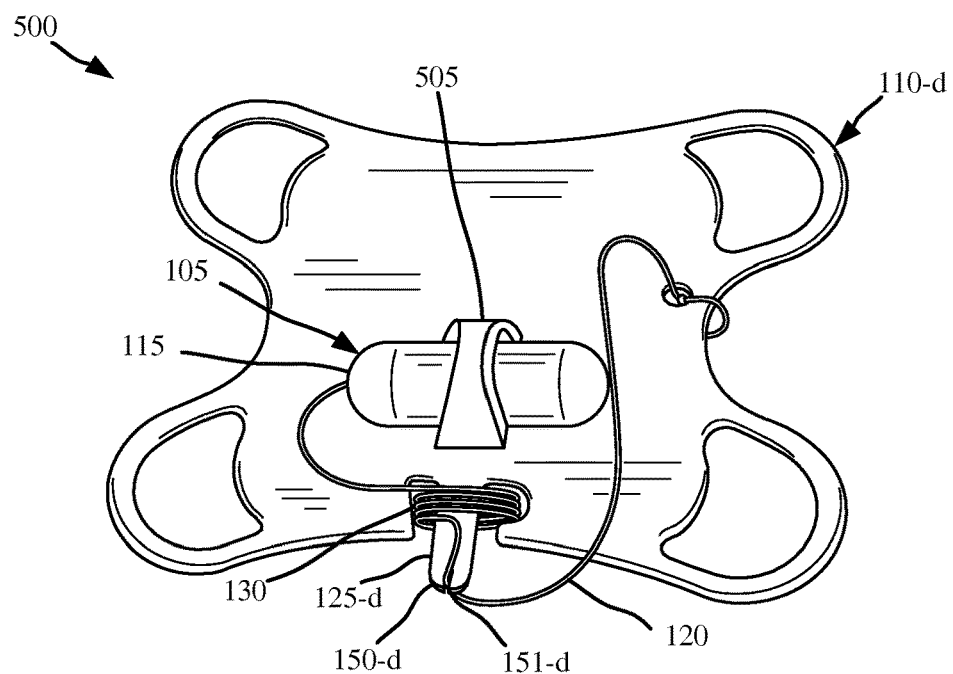
FIGS. 5A and 5B are schematic diagrams of a packaging apparatus and a swallowable cell collection device according to various embodiments.

FIG. 5A shows an example of a packaged cell collection device assembly 500 in accordance with various embodiments of the present disclosure. The cell collection device assembly 500 may include a packaging apparatus 110-*d* coupled with a cell collection device 105. The packaging apparatus 110-*d* may include a capsule housing 505 that is configured to releasably retain the swallowable capsule 115. The capsule housing 505 may either partially or fully extend around a circumference of the swallowable capsule 115 and may be sized such that the swallowable capsule 115 snugly fits within the capsule housing 505. Accordingly, the swallowable capsule 115 may be removed from the capsule housing 505 by sliding the swallowable capsule 115 out from underneath the capsule housing 505.

Additionally, the packaging apparatus 110-*d* may include one or more bundling features around which a portion of the string 120 is wrapped to form a swallowable bundle 130. For example, the packaging apparatus 110-*d* may include a shaft 125-*d* around which a portion of the string 120 may be wrapped. The shaft 125-*d* is configured to constrain the swallowable bundle 130 in a bundled configuration and to prevent the bundle 130 from sliding off the shaft 125-*d* while the cell collection device 105 is in a pre-deployed configuration. Similar to the shafts described in connection with FIGS. 1-4, the shaft 125-*d* may include a distal end retaining member 150-*d* that includes a slit 151-*d* configured to grasp a portion of string 120 to help keep the swallowable bundle 130 from sliding off of shaft 125-*d*.

Figure 5B:
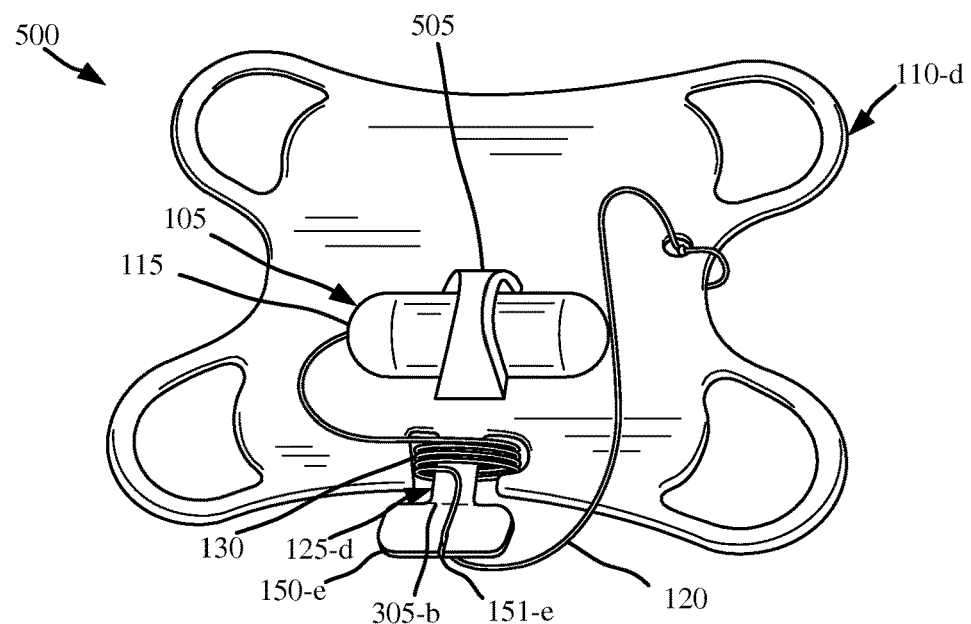

FIG. 5B shows another example of a packaged cell collection device assembly 500 in accordance with various aspects of the present disclosure. The packaging apparatus 110-*d* may be an example of the packaging apparatus 110 described in connection with any of FIGS. 1-5. The packaging apparatus 110-*d* may include a shaft 125-*d* around which a portion of string 120 may be wrapped to form a swallowable bundle 130. The shaft 125-*d* may include a distal end retaining member 150-*e* configured to prevent the swallowable bundle 130 from sliding off of shaft 125-*d*. In some examples, the distal end retaining member 150-*e* is releasably attached to shaft 125-*d* similar to the distal end retaining members 150 described in connection with FIGS. 3-4. A perforation 305-*b* may be included on shaft 125-*d* to facilitate removal of the distal end retaining member 150-*e*. Furthermore, distal end retaining member 150-*e* may include a slit 151-*e* configured to grasp a portion of string 120.

Figure 6:
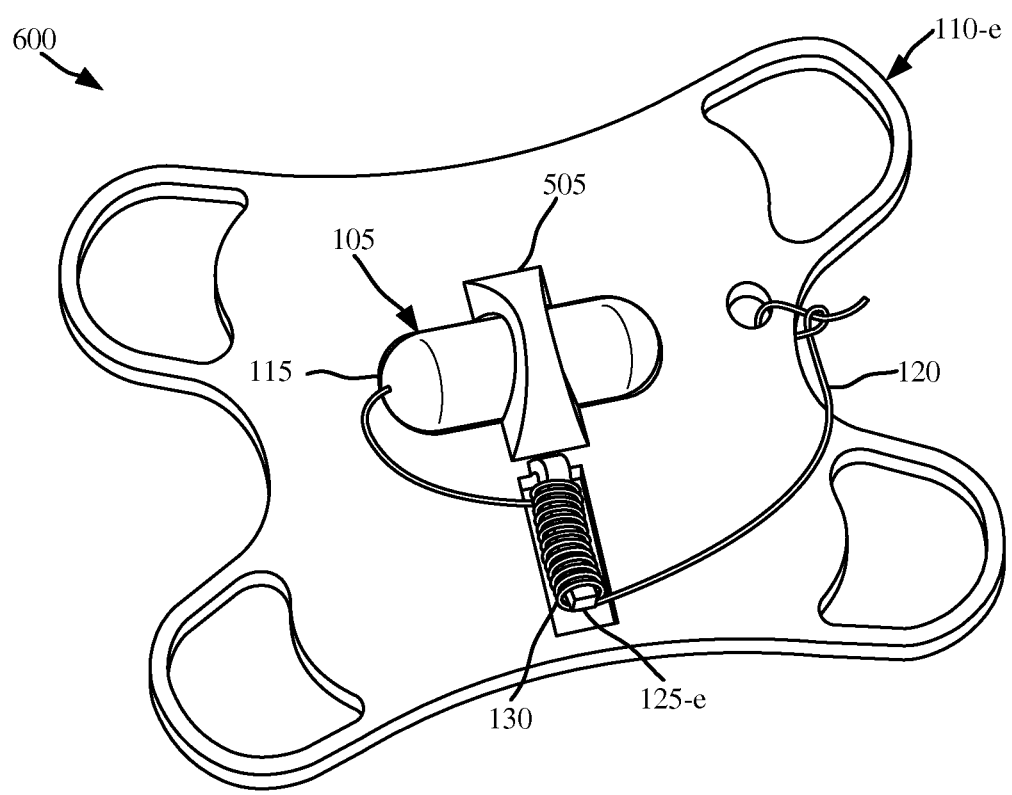
FIG. 6 is a schematic diagram of a packaging apparatus and a swallowable cell collection device according to various embodiments.

FIG. 6 shows another example of a packaged cell collection device assembly 600 in accordance with various aspects of the present disclosure. The cell collection device assembly 600 includes a packaging apparatus 110-*e* configured to facilitate the administration of a cell collection device 105 to a patient. The packaging apparatus 110-*e* may be an example of any packaging apparatus 110 described in connection with any of FIGS. 1-5. The packaging apparatus 110-*e* may include a capsule housing 505 that is configured to releasably retain the swallowable capsule 115. In addition, the packaging apparatus 110-*e* may include a wavy or curved shaft 125-*e* around which a portion of the string 120 may be wrapped to form a swallowable bundle 130. The curved shaped of the shaft 125-*e* may be configured to facilitate easy removal of the swallowable bundle 130 from the shaft 125-*e*. In addition, the curvature of the shaft 125-*e* may be configured to prevent the swallowable bundle 130 from sliding off of the shaft 125-*e*. Moreover, the shaft 125-*e* may include one or more retention features to prevent the swallowable bundle 130 from sliding off of the shaft 125-*e* while the cell collection device 105 is in a pre-deployed configuration.

Figure 7:
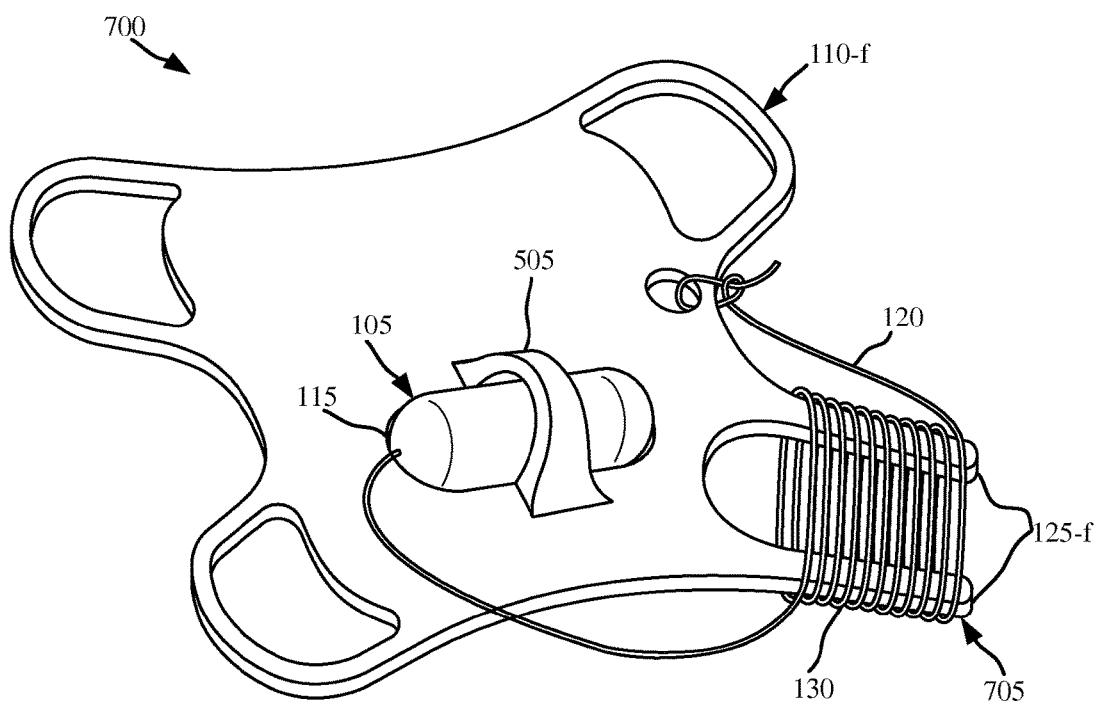
FIG. 7 is a schematic diagram of a packaging apparatus and a swallowable cell collection device according to various embodiments.

FIG. 7 shows another example of a packaged cell collection device assembly 700 in accordance with various aspects of the present disclosure. The cell collection device assembly 700 includes a packaging apparatus 110-*f* configured to facilitate the administration of a cell collection device 105 to a patient. The packaging apparatus 110-*f* may be an example of any packaging apparatus 110 described in connection with any of FIGS. 1-6. The packaging apparatus 110-*f* may include a capsule housing 505 that is configured to releasably retain a swallowable capsule 115. The packaging apparatus 110-*f* may also include a U-shaped bundling feature 705 around which a portion of string 120 may be wrapped to form a swallowable bundle 130. The U-shaped bundling feature 705 may include two shafts 125-*f* arranged in a horseshoe configuration. Each shaft 125-*f* may be an example of a shaft 125 discussed in previous embodiments and may include one or more retention features to prevent the swallowable bundle 130 from sliding off of the U-shaped bundling feature 705. The gap between the two shafts 125-*f* of the U-shaped bundling feature 705 may allow a user to easily grasp the swallowable bundle 130 between two fingers and then remove the bundle 130 from the U-shaped bundling feature 705.

Figure 8:
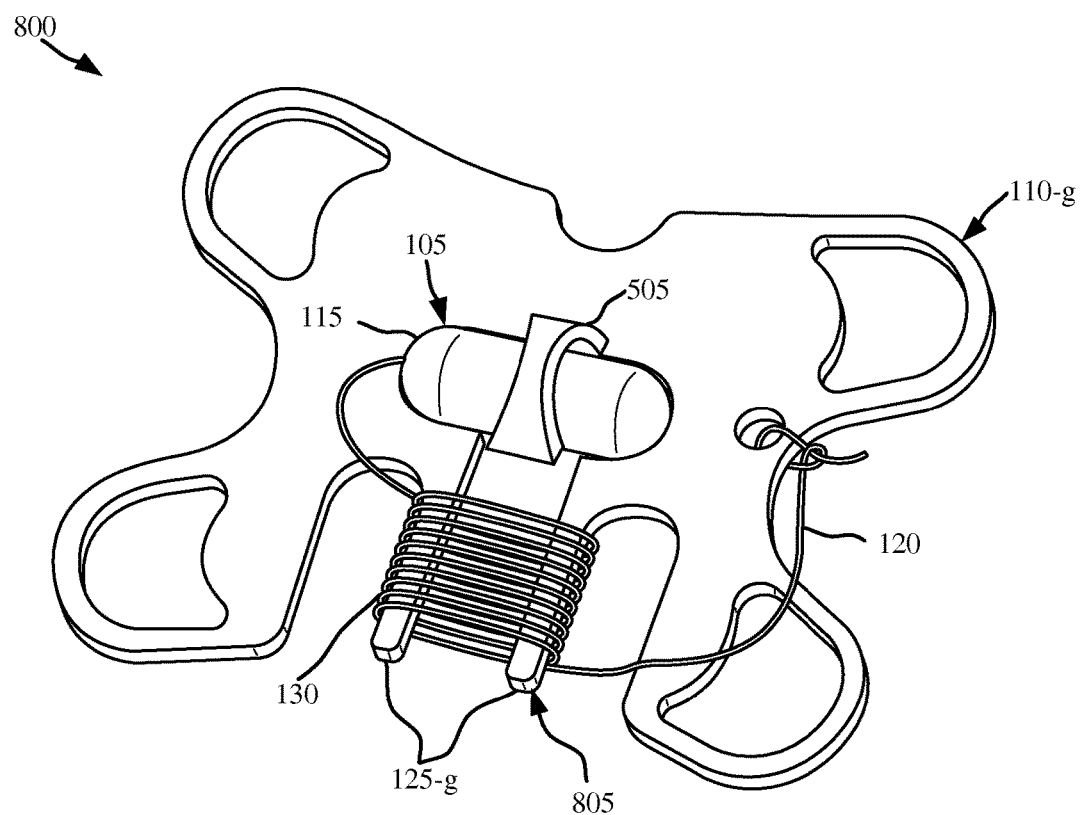
FIG. 8 is a schematic diagram of a packaging apparatus and a swallowable cell collection device according to various embodiments.

FIG. 8 shows another example of a packaged cell collection device assembly 800 in accordance with various aspects of the present disclosure. The cell collection device assembly 800 includes a packaging apparatus 110-*g* configured to facilitate the administration of a cell collection device 105 to a patient. The packaging apparatus 110-*g* may be an example of any packaging apparatus 110 described in connection with any of FIGS. 1-7. The packaging apparatus 110-*g* may include a capsule housing 505 that is configured to releasably retain the swallowable capsule 115. The packaging apparatus 110-*g* may also include a bundling feature 805 around which a portion of string 120 may be wrapped to form a swallowable bundle 130. The bundling feature 805 may include two shafts 125-*g* arranged in parallel with each other. The shafts 125-*g* may be an example of a shaft 125 described with reference to previous embodiments and may also include retention features to prevent the swallowable bundle 130 from sliding off of the bundling feature 805 while the cell collection device 105 is in a pre-deployed configuration. The gap between the two shafts 125-*g* of the bundling feature 805 may allow a user to easily grasp the swallowable bundle 130 between two fingers and then remove the bundle 130 from the bundling feature 805.

Figure 9:
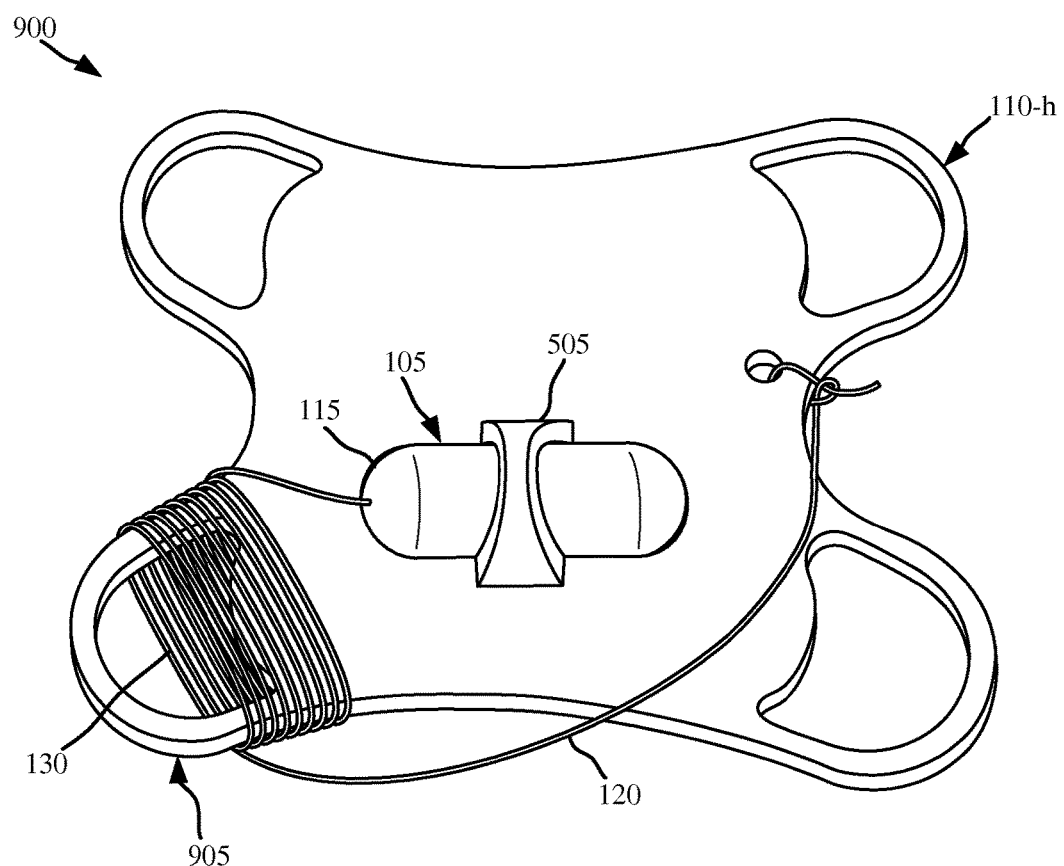
FIG. 9 is a schematic diagram of a packaging apparatus and a swallowable cell collection device according to various embodiments.

FIG. 9 shows another example of a packaged cell collection device assembly 900 in accordance with various aspects of the present disclosure. The cell collection device assembly 900 includes a packaging apparatus 110-*h* configured to facilitate the administration of a cell collection device 105 to a patient. The packaging apparatus 110-*h* may be an example of any packaging apparatus 110 described in connection with any of FIGS. 1-8. The packaging apparatus 110-*h* may include a capsule housing 505 that is configured to releasably retain the swallowable capsule 115. As shown in FIG. 9, the portion of the string 120 may be bundled around a portion of the packaging apparatus 110-*h* instead of a shaft, post, or similar bundling feature. For instance, a portion of the string 120 may be wrapped around a corner 905 of the packaging apparatus 110-*h* to form a swallowable bundle 130. Such a configuration may reduce the number of individual features or elements that need to be manufactured on the packaging apparatus 110-*h*.

Figure 10:
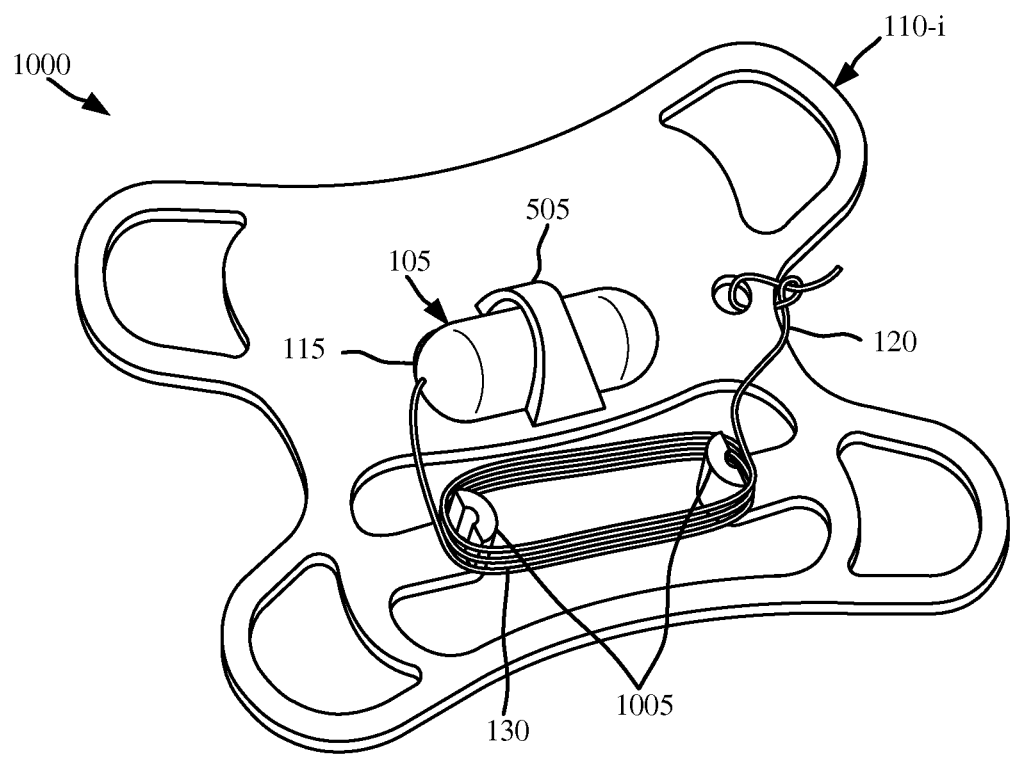
FIG. 10 is a schematic diagram of a packaging apparatus and a swallowable cell collection device according to various embodiments.

FIG. 10 shows another example of a packaged cell collection device assembly 1000 in accordance with various aspects of the present disclosure. The cell collection device assembly 1000 includes a packaging apparatus 110-*i* configured to facilitate the administration of a cell collection device 105 to a patient. The packaging apparatus 110-*i* may be an example of any packaging apparatus 110 described in connection with any of FIGS. 1-9. The packaging apparatus 110-*i* may include a capsule housing 505 that is configured to releasably retain the swallowable capsule 115. The packaging apparatus 110-*i* may also include a plurality of bundling features 1005 around which a portion of string 120 may be wrapped to form a swallowable bundle 130. In some embodiments, the bundling features 1005 may include posts that extend orthogonal to the surface of the packaging apparatus 110-*i*. The posts may be straight or slightly curved away from each other to more securely retain the swallowable bundle 130 while the cell collection device 105 is in a pre-deployed configuration. Moreover, in some embodiments, the bundling features 1005 may include other retention features similar to the shafts 125 discussed with reference to other embodiments that are configured to prevent the swallowable bundle 130 from sliding off of the free end of the bundling features 1005.

Figure 11A:
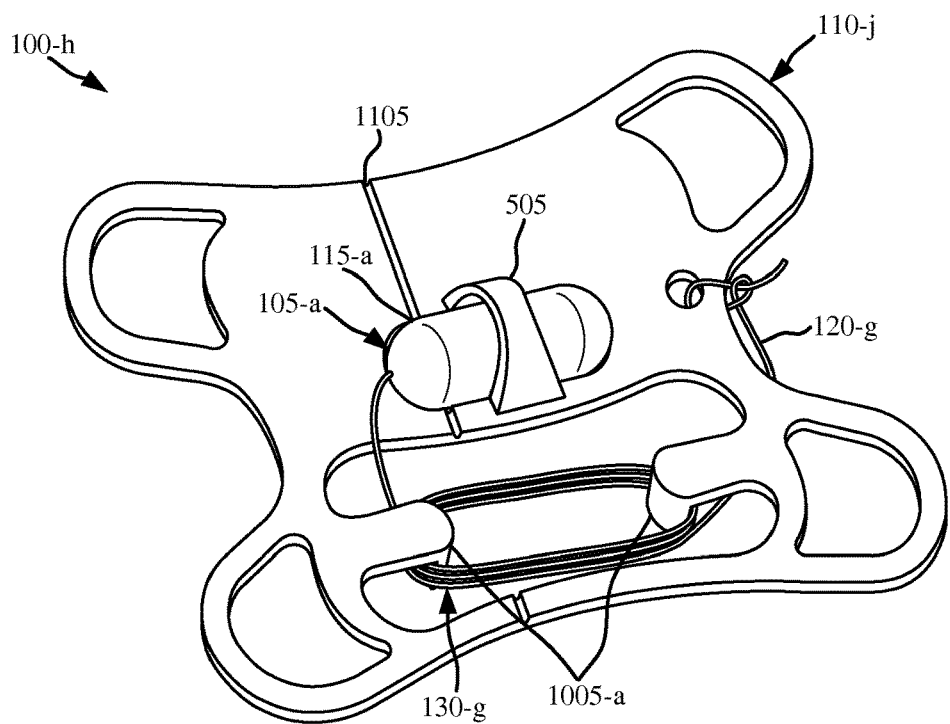
FIGS. 11A and 11B are schematic diagrams of a packaging apparatus and a swallowable cell collection device according to various embodiments.

FIG. 11A shows another example of a packaged cell collection device assembly 1100 in accordance with various aspects of the present disclosure. The cell collection device assembly 1100 includes a packaging apparatus 110-*j* configured to facilitate the administration of a cell collection device 105 to a patient. The packaging apparatus 110-*j* may be an example of any packaging apparatus 110 described in connection with any of FIGS. 1-10. The packaging apparatus 110-*j* may include a capsule housing 505 that is configured to releasably retain the swallowable capsule 115. In addition, the packaging apparatus 110-*j* may include a plurality of bundling features 1005-*a* around which a portion of string 120 may be wrapped to form a swallowable bundle 130. For example, the bundling features 1005-*a* may be include a plurality of posts around which the string 120 may be wrapped to form the swallowable bundle 130. The packaging apparatus 110-*j* may also include a scoring feature 1105 disposed on a surface of the packaging apparatus 110-*j* along which the packaging apparatus 110-*j* may bend or break when a bending force is applied to the packaging apparatus 110-*j*.

Figure 11B:
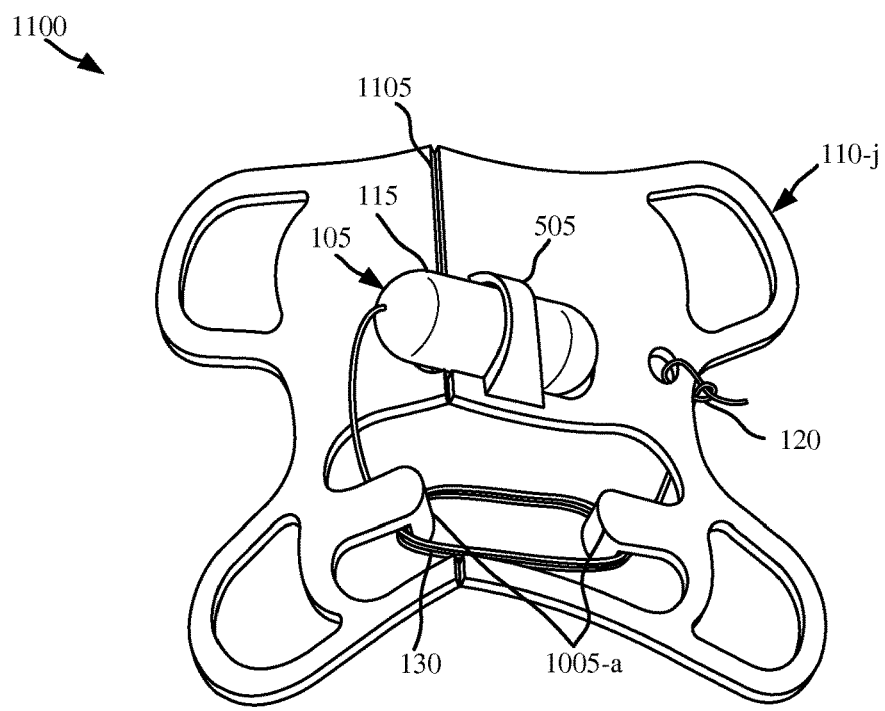

FIG. 11B shows the collection device assembly 1100 in a deployed configuration in accordance with various aspects of the present disclosure. As illustrated, a user may apply a bending force to the packaging apparatus 110-*j* until the packaging apparatus bends or breaks along the scoring feature 1105. Once the packaging apparatus 110-*j* has been sufficiently bent, the user may remove the swallowable bundle 130 from the bundling features 1005-*a* and the swallowable capsule 115 from the capsule housing 505.

FIG. 12 shows another example of a packaged cell collection device assembly 1200 in accordance with various aspects of the present disclosure. The cell collection device assembly 1200 includes a packaging apparatus 110-*k* configured to facilitate the administration of a cell collection device 105 to a patient. The packaging apparatus 110-*k* may be an example of any packaging apparatus 110 described in connection with any of FIGS. 1-11. The packaging apparatus 110-*k* may include a capsule housing 505-*a*.

As shown in FIG. 12, the capsule housing 505-*a* may be configured to releasably retain both the swallowable capsule 115 and the swallowable bundle 130 while the cell collection device 105 is in a pre-deployed configuration. In such a configuration, the string 120 may be folded back onto itself several times to form a swallowable bundle 130. The capsule housing 505-*a* may retain the swallowable bundle 130 in a bundled configuration by squeezing or sandwiching the swallowable bundle 130 between the swallowable capsule 115 and the capsule housing 505-*a* or another portion of the packaging apparatus 110-*k*. Accordingly, given the close proximity of the swallowable bundle 130 and the swallowable capsule 115, the capsule housing 505-*a* facilitates the simultaneous grasping and removal of both the swallowable capsule 115 and the swallowable bundle 130. For example, a user may simultaneously grab both the swallowable capsule 115 and the swallowable bundle 130 between two fingers or with tweezers or any other suitable grasping member and place both the swallowable capsule 115 and the swallowable bundle 130 on the tongue of a patient.

The capsule housing 505-*a* may releasably retain the swallowable capsule 115 by partially surrounding the swallowable capsule 115. For instance, the capsule housing 505-*a* may include one or more curved finger elements which extend partially around the swallowable capsule 115 thereby applying a force to retain the swallowable capsule 115 and the swallowable bundle 130 in a pre-deployed configuration. The fingers of the capsule housing 505-*a* may be elastic or malleable such that they bend as the swallowable capsule 115 is removed. In some embodiments, the capsule housing 505-*a* is made from the same material as the rest of the packaging apparatus 110-*k*. However, in other embodiments, the capsule housing 505-*a* may be made from a different material and adhered or otherwise coupled with the packaging apparatus 110-*k*. In some embodiments, the packaging apparatus 110-*k* may include a recessed portion in which the swallowable capsule 115 and the swallowable bundle 130 are partially nestled.

FIG. 13 shows another example of a packaged cell collection device assembly 1300 in accordance with various aspects of the present disclosure. The cell collection device assembly 1300 includes a packaging apparatus 110-*l* configured to facilitate the administration of a cell collection device 105 to a patient. The packaging apparatus 110-*l* may be an example of any packaging apparatus 110 described in connection with any of FIGS. 1-12. The packaging apparatus 110-*l* may also include a capsule housing 505-*b* configured to releasably retain both the swallowable cell collection device 115 and a swallowable bundle 130. The capsule housing 505-*b* may include an enclosed dome-like structure where the swallowable bundle 130 may be housed. For instance, the string 120 may be bundled by wrapping the string 120 into a ball and placing the swallowable bundle 130 into the capsule housing 505-*b*. The swallowable bundle 130 may be held in place by the swallowable capsule 115. In this way, the swallowable bundle 130 may be maintained in a bundled form while stored in the packaging apparatus 110-*l*. Upon removal of the swallowable capsule 115, the user may grasp the swallowable bundle 130 using tweezers or similar grasping techniques.

In another embodiment of the present disclosure, a bundling material may be used to form and retain a portion of the string 120 of the cell collection device 105 into a swallowable bundle 130 without the use of a shaft 125 or other bundling feature or apparatus to wrap the string 120 around. Instead, the bundling material may wrap around the string 120 or adhere to the string 120 in such a way as to retain the string 120 in a swallowable bundle 130.

Figure 14:
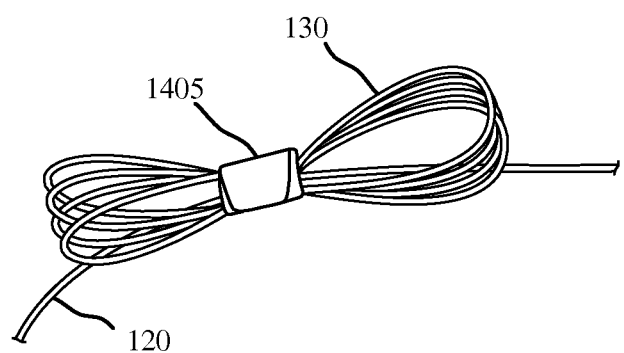
FIG. 14 is a schematic diagram of a swallowable bundle of retrieval string of a swallowable cell collection device according to various embodiments.

For example, FIG. 14 shows a string 120 of a cell collection device 105 (not shown) formed into a swallowable bundle 130 by a bundling material in the form of a band 1405. As shown in FIG. 14, the swallowable bundle 130 may be formed by looping or folding the string 120 back on itself several times. The swallowable bundle 130 may be secured near the center of the bundle 130 by the band 1405.

In some embodiments, the band 1405 is configured to release the swallowable bundle 130 passively. Passively releasing the swallowable bundle 130 refers to a means where the user does not have to actively remove the bundling material from the swallowable bundle 130 by tearing, unwrapping, or the like. For example, the band 1405 may be made from a material that dissolves when it contacts a liquid such as saliva or swallowed water. Therefore, the band 1405 would passively release the swallowable bundle 130 after dissolving. In some embodiments, the band 1405 is made from one or more hydrophilic or water-soluble polymers. Furthermore, the physical characteristics of the band 1405 may be tailored such that the band 1405 dissolves in a desired amount of time when placed on the tongue of a patient. The dissolution time of the band 1405 may be further tailored by varying the material characteristics of the band material. For example, the band material may be configured to dissolve faster in the presence of warm water or a specific chemical solution that is swallowed by the patient immediately after placing the swallowable bundle 130 on the tongue of the patient as part of the swallowing of the device. Furthermore, the thickness can be varied to control dissolution rate. In certain examples, the thickness of the band 1405 may be 1.5 mils (0.0015 inches). However, the thickness may range from 1 mils (0.001 inches) to approximately 20 mils (0.020 inches).

The band 1405 may be made from natural or synthetic materials, and may be formed either as a single polymer or as a combination of two or more polymers. Pullulan, a polysaccharide often used in the manufacture of edible films for oral hygiene strips, is an example of a suitable material. Hydroxypropyl methylcellulose (HPMC) and polyvinyl alcohol (PVA), or a combination of microcrystalline cellulose and maltodextrin are other examples of materials that could be used. In certain examples, the band 1405 can be formed into flat film strips by a solvent casting method then looped and joined into a band 1405 by either heating or adhering the ends of the flat film together. In other examples, the band 1405 may be formed as a complete band by casting onto a mandrel, or extruding the material into a tubular shape using a hot melt extrusion technique.

The composition of the band material may be manipulated to formulate a material with desired flexibility, strength, and brittleness. For example, plasticizer may be added to the formulation to improve flexibility and reduce the brittleness of the band material. Examples of suitable plasticizer excipients include glycerol, propylene glycol, low molecular weight polyethylene glycols, phthalate derivatives such as dimethyl, diethyl, and dibutyl phthalate, citrate derivatives such as tributyl, triethyl, acetyl citrate, triacetin and castor oil. Furthermore, stabilizing and thickening agents may be included in the formulation of the band material to improve the viscosity and consistency of dispersion or preparation solution or suspension before casting.

In certain embodiments, the bundling material may adhere to the retrieval string 120 to form the swallowable bundle 130 when the cell collection device 105 is in a pre-deployed configuration. For example, instead of the bundling material wrapping around the bundle 130 like a band 1405, the bundling material may encase either a portion or the entire bundle 130 to constrain the string 120 in a swallowable configuration. The bundling material may be applied to the pre-formed swallowable bundle 130 by dipping the bundle 130 in the bundling material or by pouring the bundling material over the bundle 130 of string 120. The swallowable bundle 130 may take the form of any of the configurations discussed above, such as a helical, folded, looped, and/or a ball configuration. Furthermore, the bundling material may be dissolvable and configured to release the string 120 from the swallowable bundle 130 by dissolving when placed in contact with liquid. Any suitable dissolvable material may be used, including any of the dissolvable materials discussed above in connection with FIG. 14.

Figure 15A:
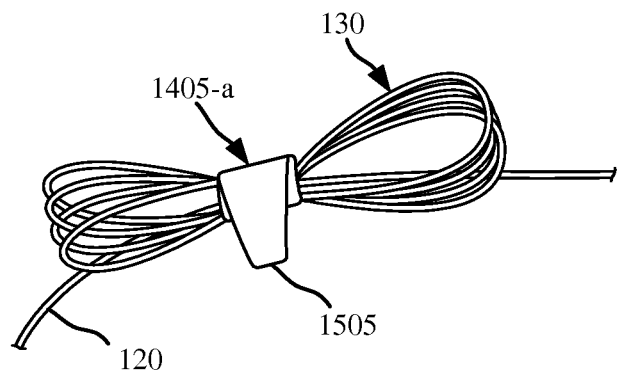
FIGS. 15A and 15B are schematic diagrams of a swallowable bundle of retrieval string of a swallowable cell collection device according to various embodiments.

FIG. 15A shows another example of a band 1405-*a* configured to retain a string 120 of a cell collection device 105 (not shown) in a swallowable bundle 130 in accordance with various aspects of the present disclosure. The band 1405-*a* may be configured to release the swallowable bundle 130 by an active process such as being torn, broken, or unwrapped. In certain examples, the band 1405-*a* is made from a material that can be easily torn or broken when pulled on by a user with a sufficient amount of force. For example, a low durometer polyurethane or silicone may be used such that the band 1405-*a* will stretch then break when pulled on. The thickness and chemical properties of the band material may be tailored to achieve a desired strength of the band 1405-*a*. In certain embodiments, the band 1405-*a* may further include a pull tab 1505 to facilitate the grip and pulling of the band 1405-*a*.

Figure 15B:
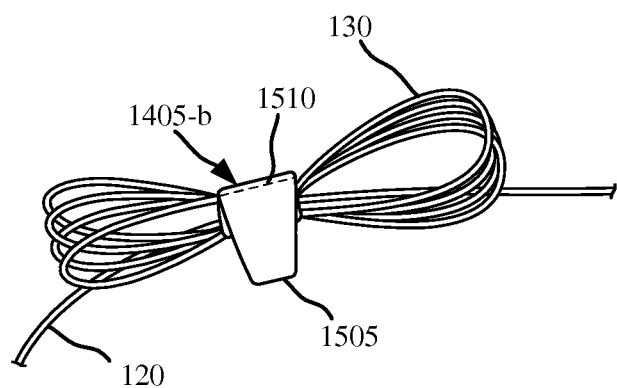

As shown in FIG. 15B, in some aspects of the present disclosure, the band 1405-*b* may include a perforation or other intentional weakness such that the band 1405-*b* will break at a desired location under the desired amount of force or stress. For example, the band 1405-*b* may include a perforation 1510. The band 1405-*b* may also include a pull tab 1505-*a* to facilitate the grip and tearing of the band 1405-*b* along the perforation 1510.

In other embodiments, the band 1405 is configured to unwrap from around the swallowable bundle 130 without breaking or tearing. For example the band 1405 may be initially wrapped around the bundle 130 and secured to itself with an adhesive or other attachment means. When the band 1405 is pulled with sufficient force, the adhesive or other attachment means may break allowing the band 1405 to be unwrapped. Some embodiments include a pull tab 1505 to facilitate gripping and unwrapping the band 1405, as shown in FIG. 15A.

Figure 16:
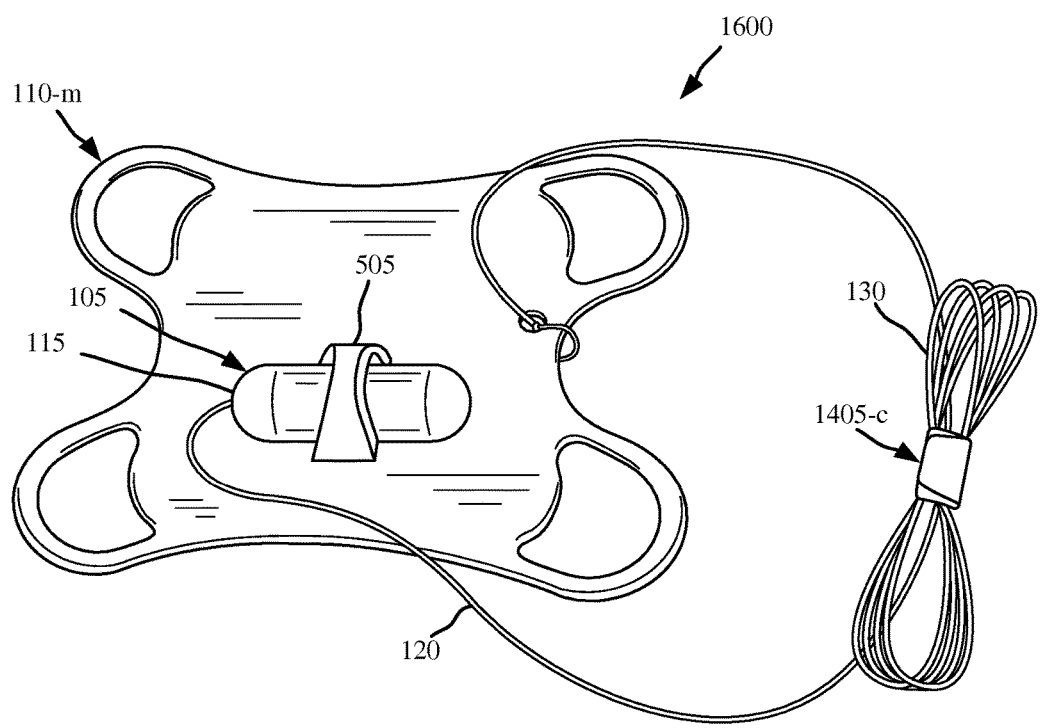
FIG. 16 is a schematic diagram of a packaging apparatus and a swallowable cell collection device according to various embodiments.

FIG. 16 shows another example of a packaged cell collection device assembly 1600 in accordance with various aspects of the present disclosure. The cell collection device assembly 1600 includes a packaging apparatus 110-*m* configured to facilitate the administration of a cell collection device 105 to a patient. The packaging apparatus 110-*m* may be an example of any packaging apparatus 110 described in connection with any of FIGS. 1-13. The packaging apparatus 110-*m* may also include a capsule housing 505 configured to releasably retain the swallowable capsule 115 of the cell collection device 105. As shown in FIG. 16, any of the bands 1405 discussed with reference to FIGS. 14-15 may be combined with a packaging apparatus 110 to retain the string 120 in a swallowable bundle 130 while the cell collection device 105 is in a pre-deployed configuration. For instance, the swallowable bundle 130 may be retained by a band 1405-*c* that is detached from the packaging apparatus 110-*m*. The band 1405-*c* may be an example of any of the bands 1405 described in connection with any of FIGS. 14-15.

Figure 17:
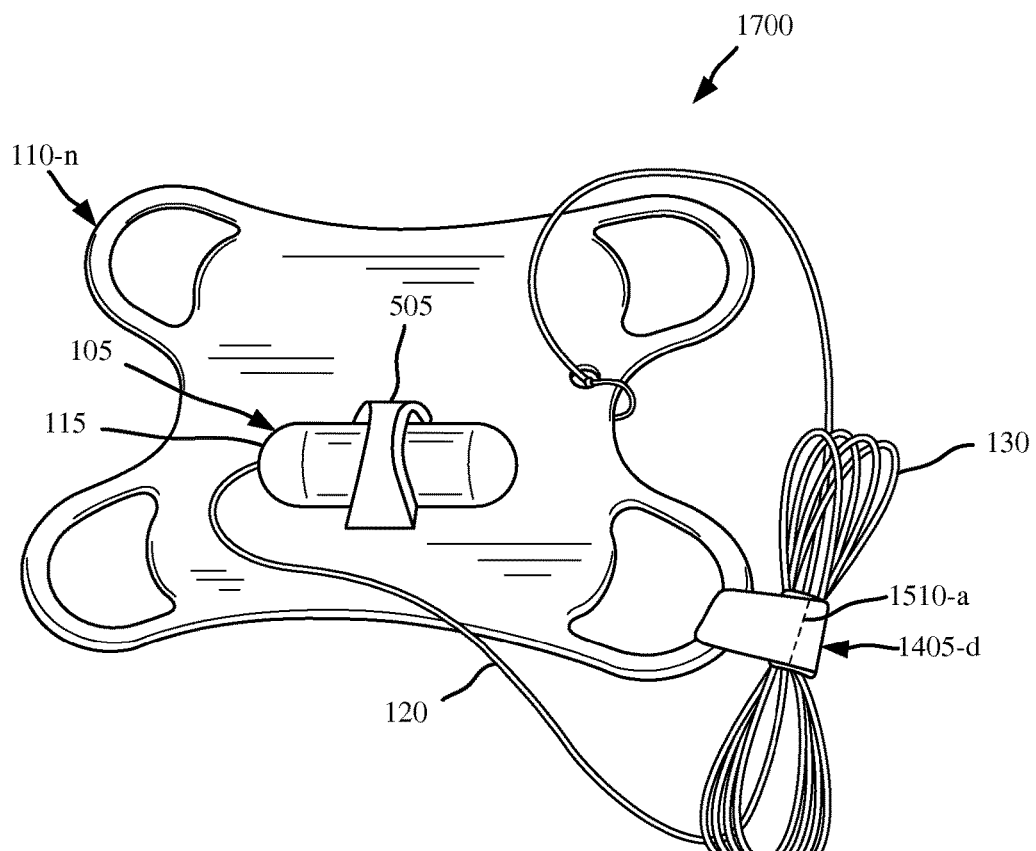
FIG. 17 is a schematic diagram of a packaging apparatus and a swallowable cell collection device according to various embodiments.

FIG. 17 shows another example of a packaged cell collection device assembly 1700 in accordance with various aspects of the present disclosure. The cell collection device assembly 1700 includes a packaging apparatus 110-*n* configured to facilitate the administration of a cell collection device 105 to a patient. The packaging apparatus 110-*n* may be an example of any packaging apparatus 110 described in connection with any of FIGS. 1-13 and 16. The packaging apparatus 110-*n* may include a capsule housing 505 that is configured to releasably retain the swallowable capsule 115. As shown in FIG. 17, the band 1405-*d* may be coupled with the packaging apparatus 110-*n*. The band 1405-*d* may be an example of any of the bands 1405 described in connection with any of FIGS. 13-14. The band 1405-*d* may be configured such that when a user pulls on the bundle 130, the band 1405-*d* unwraps, tears or otherwise breaks to release the swallowable bundle 130 from the band 1405-*d* while the band 1405-*d* remains attached to the packaging apparatus 110-*n*. For example, the band 1405-*d* may include a perforation 1510-*a* or similar feature to facilitate the breaking or tearing of the band 1405-*d*.

Figure 18A:
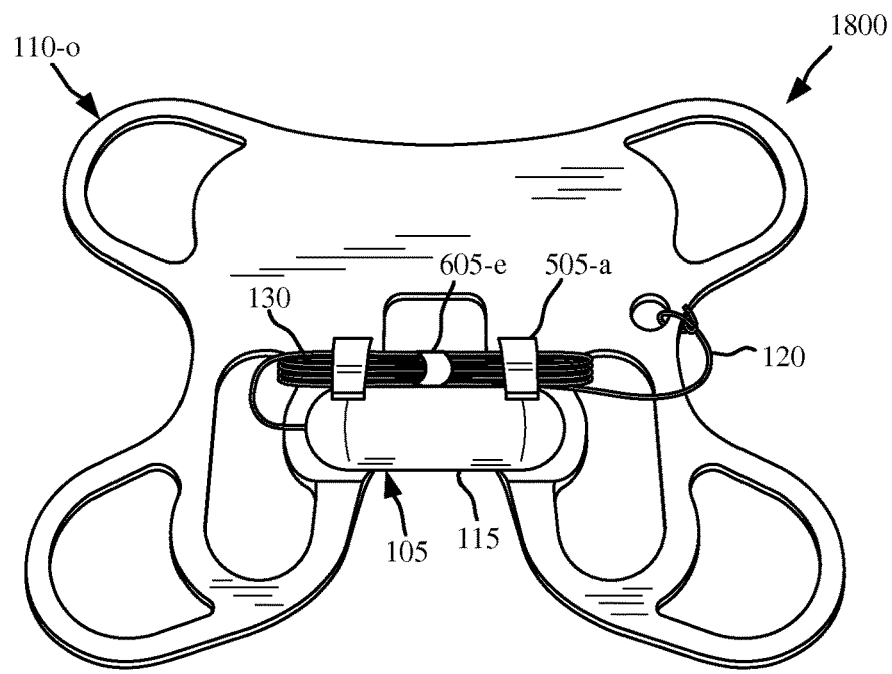
FIGS. 18A and 18B are schematic diagrams of a packaging apparatus and a swallowable cell collection device according to various embodiments.

FIG. 18A shows another example of a packaged cell collection device assembly 1800 in accordance with various aspects of the present disclosure. The cell collection device assembly 1800 includes a packaging apparatus 110-*o* configured to facilitate the administration of a cell collection device 105 to a patient. The packaging apparatus 110-*o* may be an example of any packaging apparatus 110 described in connection with any of FIGS. 1-13 and 16-17. Similar to the embodiment described with reference to FIG. 12, the packaging apparatus 110-*o* may include a capsule housing 505-*a* that is configured to releasably retain both a swallowable capsule 115 and a swallowable bundle 130. In addition to being sandwiched between the swallowable capsule 115 and the capsule housing 505-*a*, the swallowable bundle 130 may be confined to a bundled configuration with a band 1405-*e*. The band 1405-*e* may be an example of any band 1405 described with reference to FIGS. 14-17. In such a configuration, a user may simultaneously grasp the swallowable capsule 115 and the swallowable bundle 130 and remove them from the capsule housing 505-*a*. Then, depending on the type of band 1405-*e* used, the user may break the band 1405-*e* to release the swallowable bundle 130 prior to placing it on the patient's tongue, or the band 1405-*e* may be configured to dissolve after being placed on the patient's tongue.

Figure 18B:
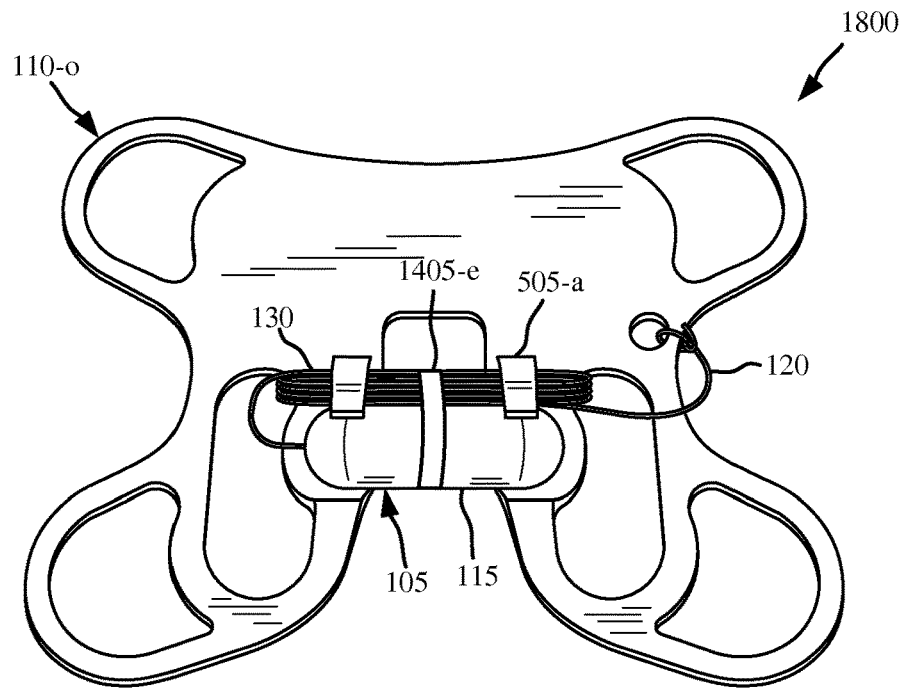

FIG. 18B shows another example of a packaged cell collection device assembly 1800 described with reference to FIG. 18A. However, in this embodiment, a band 1405-*f* is configured to wrap around both the swallowable bundle 130 and the swallowable capsule 115. The band 1405-*f* may be an example of any band 1405 described with reference to FIGS. 14-18A. Accordingly, a user may simultaneously grasp both the swallowable bundle 130 and the swallowable capsule 115 and remove them from the capsule housing 505-*a*. Then, depending on the type of band 1405-*f* used, the user may break the band 1405-*f* to release the swallowable bundle 130 prior to placing it on the patient's tongue, or the band 1405-*f* may be configured to dissolve after being placed on the patient's tongue.

Figure 19:
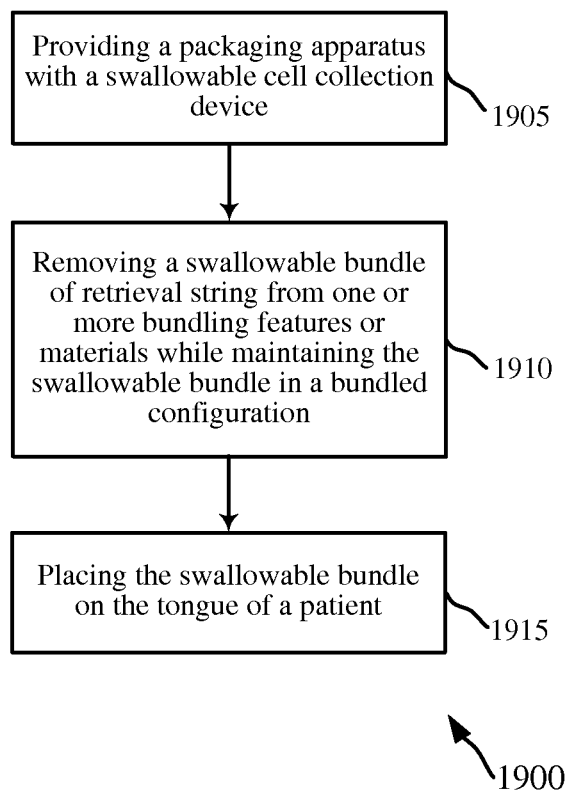
FIG. 19 is a flowchart of a method for administering a swallowable cell collection device to a patient according to various embodiments.

Methods for administering a cell collection device 105 to a patient using a packaging apparatus 110 are now described. FIG. 19 shows a flowchart of a method 1900 for administering a swallowable cell collection device 105 to a patient in accordance with various aspects of the present disclosure. For clarity, the method 1900 is described with reference to aspects of one or more apparatuses described in connection with the previous figures.

At block 1905, a user provides a packaging apparatus 110 with a swallowable cell collection device 105. The swallowable capsule 115 of the cell collection device 105 is releasably retained in a capsule housing 505. Moreover, a portion of retrieval string 120 is releasably retained in a swallowable bundle 130 by one or more bundling features or bundling materials.

At block 1910, the user removes the swallowable bundle 130 from the one or more bundling features or bundling materials. In certain embodiments, the one or more bundling features are one or more shafts 125, corners 905, or posts 1005 around which the swallowable bundle 130 is wrapped, as is described in connection with any of FIGS. 1-11. In accordance with these embodiments, removing the swallowable bundle 130 from the bundling features may include sliding the swallowable bundle 130 of off the bundling feature such as from the distal end of the shaft 125. Removing the swallowable bundle 130 may additionally include removing a distal end retaining member 150 or removing a portion of the retrieval string 120 from a slit 151 in the distal end retaining member 150 before sliding the swallowable bundle 130 from the shaft 125 as is described in connection with any of FIGS. 1-8. In some embodiments, the bundling features comprises a capsule housing 505-*a* that retains the swallowable bundle 130 by sandwiching the swallowable bundle 130 between a swallowable capsule 115 and the capsule housing 505-*a* as described with reference to FIGS. 12 and 18. In such embodiments, removing the swallowable bundle 130 from the one or more bundling features may include removing both the swallowable capsule 115 and the swallowable bundling 130 from the capsule housing 505-*a*.

In yet other embodiments of the present disclosure, the swallowable bundle 130 is releasably retained by a bundling material such as a band 1405, as is described in connection with any of FIGS. 14-18. In accordance with these embodiments, removing the swallowable bundle 130 from the bundling material may include tearing and/or unwrapping the band 1405 from around the swallowable bundle 130. In certain examples, tearing and/or unwrapping the band 1405 may include pulling on a pull tab 1505 of the band 1405 as is described in connection with FIG. 15. Furthermore, tearing the band 1405 may be facilitated by a perforation 1510 or other weakness included in the band 1405 as is described in connection with FIGS. 15 and 17.

Regardless of the type of bundling feature or material or the method for releasing the swallowable bundle 130 from the bundling feature, the user maintains the string 120 in a swallowable bundle 130 while releasing the swallowable bundle 130 from the bundling features or materials. Accordingly, there is no need to rewrap or re-bundle the string 120 into a swallowable bundle 130. The user may retain the swallowable bundle 130 in a swallowable configuration by grasping the swallowable bundle 130 between two fingers, such as the index finger and thumb, or any other suitable grasping device such as tweezers.

At block 1915, the user places the swallowable bundle 130 on the tongue of a patient. The swallowable bundle 130 may be placed on the tongue with the fingers of the user or with tweezers or any other suitable grasping device. In certain examples, the swallowable bundle 130 is placed on the tongue contemporaneously with the swallowable capsule 115.

Figure 20:
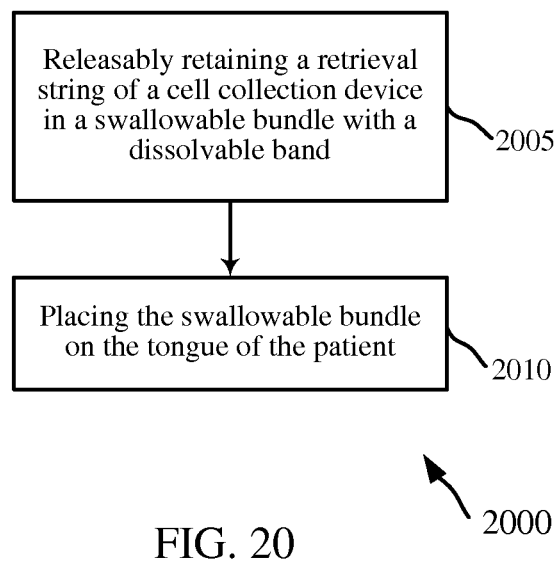
FIG. 20 is a flowchart of a method for administering a swallowable cell collection device to a patient according to various embodiments.

FIG. 20 shows a flowchart of a method 2000 for administering a swallowable cell collection device 105 to a patient in accordance with various aspects of the present disclosure. At block 2005, a retrieval string 120 of a cell collection device 105 is constrained in a swallowable bundle 130 with a dissolvable band 1405. The dissolvable band 1405 may be an example of any of the bands 1405 described in connection with FIGS. 14-18.

At block 2010, the user places the swallowable bundle 130 on the tongue of the patient. The dissolvable band 1405 then dissolves on the tongue of the patient and releases the string 120 from the swallowable bundle 130 as the swallowable bundle 130 is being swallowed. The swallowable bundle 130 may be placed on the tongue of a patient with the fingers of the user or with tweezers or any other suitable grasping device. In some embodiments, the swallowable bundle 130 is placed on the tongue contemporaneously with the swallowable capsule 115.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. A packaging apparatus for administering a swallowable cell collection device to a patient, comprising:
the swallowable cell collection device, the swallowable cell collection device comprising a swallowable capsule coupled with a retrieval string;
a capsule housing configured to releasably retain the swallowable capsule; and
a bundling material configured to releasably retain a portion of the retrieval string in a swallowable bundle, wherein the bundling material is wrapped around at least the portion of the retrieval string is bundled and positioned with respect to the swallowable capsule such that the swallowable capsule housing is configured to facilitate simultaneous grasping and removal of the bundled retrieval string and the swallowable capsule from the packaging apparatus.

2. The packaging apparatus of claim 1, wherein the bundling material is a band.

3. The packaging apparatus of claim 1, wherein the bundling material is coupled with the packaging apparatus.

4. The packaging apparatus of claim 1, wherein the bundling material is dissolvable such that it dissolves when placed in contact with a liquid.

5. The packaging apparatus of claim 1, wherein the bundling material further comprises a pull tab.

6. The packaging apparatus of claim 1, wherein the bundling material further comprises a perforation.

* * * * *